United States Patent
Russell et al.

(10) Patent No.: US 7,666,911 B2
(45) Date of Patent: Feb. 23, 2010

(54) SELF ASSEMBLED NANOSTRUCTURES AND METHODS FOR PREPARING THE SAME

(75) Inventors: Alan J. Russell, Gibsonia, PA (US); Richard R. Koepsel, Pittsburgh, PA (US); Sang Beom Lee, Harrison City, PA (US)

(73) Assignee: NanoSembly, LLC, Harrison City, PA (US)

( * ) Notice: Subject to any disclaimer, the term of this patent is extended or adjusted under 35 U.S.C. 154(b) by 603 days.

(21) Appl. No.: 11/237,838

(22) Filed: Sep. 27, 2005

(65) Prior Publication Data

US 2007/0232699 A1    Oct. 4, 2007

Related U.S. Application Data

(63) Continuation-in-part of application No. PCT/US2005/016820, filed on May 13, 2005.

(60) Provisional application No. 60/570,785, filed on May 13, 2004.

(51) Int. Cl.
*A61K 31/16* (2006.01)
*G01N 33/544* (2006.01)
*A61K 9/127* (2006.01)
*C07C 237/00* (2006.01)
*G01N 33/53* (2006.01)

(52) U.S. Cl. .................. 514/614; 514/627; 554/52; 435/7.31; 435/7.32; 435/176; 436/535; 977/712; 977/797; 977/882; 424/450; 564/153

(58) Field of Classification Search ............ None
See application file for complete search history.

(56) References Cited

U.S. PATENT DOCUMENTS

| 4,867,917 A | 9/1989 | Schnur et al. |
| 4,877,501 A | 10/1989 | Schnur et al. |
| 5,004,566 A | 4/1991 | Schnur et al. |
| 7,175,762 B1 * | 2/2007 | Noce et al. ............ 210/500.22 |

OTHER PUBLICATIONS

Shimizu, Toshimi; Masuda, Mitsutoshi; Minamikawa, Hiroyuki; Supramolecular Nanotube Architectures Based on Amphiphilic Molecules, 2005, American Chemical Society, Chemical Reviews, vol. 105, pp. 1401-1443.*

Kunitake, Toyoki; Synthetic Bilayer Membranes: Molecular Design, Self-Organization, and Application; 1992; VCH Verlagsgesellschaft mbH; Angew. Chem. Int. Ed., vol. 31, pp. 709-726.*

Schnur, Joel, M.; Lipid Tubules: A Paradigm for Molecularly Engineered Structures; Science, vol. 262, pp. 1669-1676.*

(Continued)

*Primary Examiner*—Johann R Richter
*Assistant Examiner*—Ivan Greene
(74) *Attorney, Agent, or Firm*—The Webb Law Firm

(57) ABSTRACT

The present invention provides amphiphilic diacetylene compounds, and compositions and self-assembled nanotubes containing the same. Also provided are methods of producing the compounds, compositions, and nanotubes of the invention, and methods of destroying or inhibiting the growth or proliferation of microorganisms using the nanotubes of the present invention.

16 Claims, 9 Drawing Sheets
(1 of 9 Drawing Sheet(s) Filed in Color)

OTHER PUBLICATIONS

Cheng, Quan; Yamamoto, Maki; Stevens, Raymond C.; Amino Acid Terminated Polydiacetylene Lipid Micronstuctures: Morphology and Chromatic Transition; American Chemical Society; Langmuir, vol. 16, pp. 5333-5342.*

Singh Alok; Schoen, Paul E.; Self-assembled Microstructures from a Polymerizable Ammonium Surfactant: Di(Hexacosa-12,14-diynyl)dimethylammonium Bromide; 1988; Journal of Chemical Society, Chemical Communications; pp. 1222-1223.*

Occupational Outlook Handbook 2008-2009 ed.; Entry for Chemists and Material Scientists, US department of Labor, pp. 1-4.*

Lindsell, W. Edward; Preston, Peter N.; Seddon, John M.; Rosair, Georgina M.; Woodman, Thomas A. J.; 2002, Microscopic Helical and Cylindrical Morphologies from Achiral 1,3-Diynes; American Chemical Society; Chemistry of Materials, vol. 12, pp. 1572-1576.*

Shimizu, Toshimi; Masuda Mitsutoshi; Minamikawa, Hiroyuki; Supramolecular Nanotube Architectures Based on Amphiphilic Molecules; 2005; American Chemical Society, Chemical Reviews, vol. 105, No. 4, pp. 1401-1443.*

Schnur, Joel M.; Lipid Tubules: A Paradigm for Moleclarly Engineered Structures;1993; American Association for the Advancement of Science; Science, vol. 262, No. 5140, pp. 1669-1676.*

Cheng, Quan; Yamamoto, Maki; Stevens, Raymond C.; Amno Acid Terminated Polydiacetylene Lipid Microstructures: Morphology and Chromatic Transition; 2000; American Chemical Society; Langmuir, vol. 16, No. 12, pp. 5333-5342.*

Sang Beom Lee et al. Self-Assembly of Biocidal Nanotubes from a Single-Chain Diacetylene Amine Salt, J. Am. Chem. Soc., XXX , Mar. 17, 2004.

Alan S. Rudolph et al., Phase characteristics of positional isomers of 1,2-di(heptacosadiynoyl) . . . Biochimica et Biophysica Acta, 943 (1988) pp. 454-462.

Robert W. Carpick et al., Polydiacetylene films: a review of recent investigations into chromogenic . . . J. Phys.: Condens, Matter 16(2004) pp. R679-R697.

Serhil Pakhomov et al., Chiral tubule self-assembly from an achiral diynoic lipid, Dept. of Chem., Louisiana State Univ., Mar, 18, 2003, vol. 100, No. 6, pp. 3040-3042.

Ulrich Jonas et al., Reversible Color Switching and Unusual Solution Polymerization of Hydrazide-Modified Diacetylene Lipids; 1999 Amer. Chem. Soc. pp. 4580-4588.

Joel M. Schnur, Lipid Tubules: A Paradigm for Molecularly Engineered Structures, Science, vol. 262, Dec. 10, 1993, pp. 1669-1676.

Alok Singh et al. Self-assembled Microstructures from a Polymerizable Ammonium Surfactant: . . . Chem. Soc. Commun. 1988, pp. 1222-1223.

Jonathan V. Selinger et al., Theory of Self-Assembled Tubules and Helical Ribbons, The Journal of Physical Chemistry B. col. 105, No. 30, Aug. 2, 2001, pp. 7157-7169.

Alok Singh et al. Toward the Rational Control of Nanoscale Structures Using Chiral . . . , Amer. Chem. Soc., Dec. 19, 2002, Langmuir 2003, 19, pp. 1888-1898.

W. Edward Lindsell et al., Macroscopic Helical and Cylindrical Morphologies from Achiral 1,3-Diynes, Amer. Chem. Soc., May 18, 2000, Chem Mate, 2000 12, pp. 1572-1576.

Britt N. Thomas et al., Lipid Tubule Self-Assembly: Length Dependence on Cooling Rate Through a First-Order Phase Transition, Science, vol. 267, Mar. 17, 1995, pp. 1635-11638.

B.N. Thomas et al., Phosphonate Lipid Tubules. 1, J. Am. Chem. Soc. 1998, 120, pp. 12178-12186.

* cited by examiner

3.

200 nm

4.

200 nm

SELF ASSEMBLED NANOSTRUCTURES AND METHODS FOR PREPARING THE SAME

CROSS-REFERENCE TO RELATED APPLICATIONS

This application is a continuation in part application of and claims the benefit of international application PCT/US2005/16820, filed on May 13, 2005, which claims the benefit of U.S. Provisional Application No. 60/570,785, filed on May 13, 2004, both of which are incorporated herein by reference in their entirety.

STATEMENT OF GOVERNMENT INTEREST

This invention was made with government support under the Department of Defense Multidisciplinary University Research Initiative (MURI) Grant No. DAAD19-01-1-0619. As such, the United States government has certain rights in this invention.

FIELD OF THE INVENTION

The present invention relates generally to novel diacetylene compounds, self-assembling nanotubes and nanostructures (e.g., nanocarpets), and methods of making and using the same.

BACKGROUND OF THE INVENTION

The discovery of carbon nanotubes has attracted enormous attention over the past decade due to their potential significance in nanoelectronic devices (S. Iijima, Nature vol. 354, 56-58 (1991)). Micro and nano tubules produced from amphiphilic lipids have also captured the imagination of scientists in disciplines from biology through material science to chemistry and physics (J. M. Schnur, Science 262:1669-1676 (1993)). Tubules of this type have promises as advanced materials in a plethora of applications ranging from small molecular wires, to drug encapsulation, to biosensors. However, to date only a few classes of lipids, nearly all of which are chiral, are shown to have the capacity to form tubular structures under controlled conditions. Schnur et al., in U.S. Pat. No. 4,887,501, disclosed the use of phosphoglycerides derived from diacetylene carboxylic acids which self-assembled into tubular microstructures upon a change in solvent polarity. The tubes so formed were generally not uniform in size: although specific conditions yielded narrow distributions in diameter, tube lengths varied considerably.

There remains a need for a method of preparing tubules of uniform diameter and length. The difficulty in preparing optically active phospholipid variants is another major obstacle to the use of typical lipids and phospholipid analogues in the fabrication of lipid helices and tubules.

Various attempts have been made to overcome these problems by chemical modification of amphiphilic diacetylene lipids. Schoen et al. have discussed method of making lipid tubules composed of chiral diacetylenic phosphocholine by a cooling process (U.S. Pat. No. 4,990,291). The diacetylenic phosphocholines have distinctly different endothermic and exothermic transition temperatures. Lipid tubules can be formed by hydrating a diacetylenic phosphocholine at a temperature above its endothermic transition temperature then slowly lowering the temperature. Unlike spherical liposomes, lipid tubules reflect the chiral nature of the lipids used to form them. This chirality in molecular packing is reflected in the helical structures, often visible in electron microscopy images of the tubules, and in large peaks observed in their circular dichroism (CD) spectra. The helicity and the CD spectra of the tubules change handedness when the opposite enantiomer lipid is used.

Tubules were observed by Schoen and Yager (Mol. Cryst. Liq. Cryst. vol. 106, 371 (1984)) as having assembled in water from liposomes of the two-chain chiral lipid diacetylene, 1,2-bis(tricosa-10,12-diynoyl)-sn-glycero-3-phosphocholine ("$DC_{8,9}PC$"). Tubules formed from $DC_{8,9}PC$ have an average diameter of 0.5 µm and lengths which range from 50 to 200 µm. The size and stability of these tubules were sensitive to preparation conditions and thermal history, resulting in a non-homogenous preparation. Other work with chiral lipids bearing two diacetylenic chains has demonstrated that it is difficult to generate uniform nanotube structures from these precursors (see, e.g., Thomas et al., Science vol. 267, 1635 (1995); Spector et al., Nano Letters vol. 1, 375 (1984); Wand et al., Langmuir vol. 15, 6135 (1999); Svenson et al., Langmuir vol. 15, 4464 (1999); Seddon et al., Angew. Chem. Int. Ed. vol. 41, 2988 (2002); and Thomas et al., J. Am. Chem. Soc. vol. 124, 1227 (2002)).

Cheng et al. (Langmuir vol. 16, 5333 (2000)) and Frankel et al. (J. Am. Chem. Soc. vol. 116, 10057 (1994)) reported that compounds consisting of single, chiral diacetylenic chains can form tubules. In addition, Singh et al. (J. Chem. Soc., Chem. Commun. vol. 18, 1222 (1988)) discussed the formation of tubules from a non-chiral amphiphile composed of two diacetylenic chains, and Lindsell et al. (Chem. Mater. vol. 12, 1572 (2000)) discussed the preparation of micrometer sized tubules from non-chiral amphiphile composed of single diacetylene chain. However, the tubule-like structures discussed in these publications were quite heterogeneous.

SUMMARY OF THE INVENTION

The present invention generally provides a compound having formula (I), and salts thereof:

$$W-C\equiv C-C\equiv C-V-L-QX \qquad (I)$$

Wherein, the moiety $W-C\equiv C-C\equiv C-V$ is a bilayer-compatible hydrophobic chain;

L is a linker comprising a chain of from 1 to 10 atoms;

Q is $-NR_2$ or $-NR'R_2^+$;

X is an anion, present only when Q is $-NR'R_2^+$;

each R is independently selected from the group consisting of H, $C_1$-$C_8$ alkyl and $C_6$-$C_{10}$ aryl; each R independently being unsubstituted or substituted with one or more substituents selected from the group consisting of halogen, oxo, acyl, alkenyl, alkoxyl, alkyl, alkylamino, amino, aryl, cycloalkyl, heterocyclyl, and heterocyclylalkyl, with the proviso that at least one R is not H; and R' is $C_1$-$C_8$ alkyl, optionally substituted with at least one selected from the group consisting of halogen, oxo, acyl, alkenyl, alkoxyl, alkyl, alkylamino, amino, aryl, cycloalkyl, heterocyclyl, and heterocyclylalkyl.

The invention also provides nanostructures containing one or more compounds of formula (I).

In certain embodiments, the compound is selected from the group consisting of N-10,12-pentacosadiynoyl-N'-ethylethylenediamine hydrobromide ("compound 3"), N-10,12-pentacosadiynoyl-N',N'-diethylethylenediamine hydrobromide ("compound 4"), N-10,12-pentacosadiynoyl-N',N',N'-triethylethylenediammonium bromide ("compound 5"), N-10,12-pentacosadiynoyl-N'-ethylethylenediamine ("compound 6"), and N-10,12-pentacosadiynoyl-N',N'-diethylethylenediamine ("compound 7").

In one aspect, the present invention also provides a method for preparing a compound having formula (I), wherein W is $CH_3(CH_2)_a$- and V is —$(CH_2)_b$- and wherein a+b is from about 4 to about 30, which comprises reacting a compound having formula (II):

$$CH_3(CH_2)_a—C≡C—C≡C—(CH_2)_b—COOH \quad (II)$$

in a reaction mixture with a diamine compound having formula (III):

$$H_2N-L'-NR_2 \quad (III)$$

in the presence of a carboxylic acid activating reagent, thereby producing a compound having formula (IV):

$$CH_3(CH_2)_a—C≡C—C≡C—(CH_2)_b—CONH-L'-NR_2 \quad (IV)$$

and, optionally, reacting the compound having formula (IV) with an alkylating agent R'—Y, thereby producing the compound of formula (V), $$CH_3(CH_2)_a—C≡C—C≡C—(CH_2)_b—CONH-L'-NR'R_2^+X^- \quad (IV)$$

wherein, a+b is from about 4 to about 30;

L' is selected from the group consisting of $CH_2CH_2$, $CH_2CH_2CH_2$, and $CH_2CH_2ZCH_2CH_2$;

where Z is selected from the group consisting of $CH_2$, O, S, and NR;

X is a leaving group;

each R is independently selected from the group consisting of hydrogen, $C_1$-$C_8$ alkyl, and $C_6$-$C_{14}$ aryl, wherein each R is optionally substituted with at least one selected from the group consisting of halogen, oxo, acyl, alkenyl, alkoxyl, alkyl, alkylamino, amino, aryl, cycloalkyl, heterocyclyl, and heterocyclylalkyl; and R' is $C_1$-$C_8$ alkyl, optionally substituted with at least one selected from the group consisting of halogen, oxo, acyl, alkenyl, alkoxyl, alkyl, alkylamino, amino, aryl, cycloalkyl, heterocyclyl, and heterocyclylalkyl.

Suitable carboxylic acid activating reagents are well-known in the art, and include but are not limited to carbodiimides, thionyl chloride, and oxalyl chloride, and preferably include catalysts such as N-hydroxysuccinimide, N-hydroxybenzotriazole, and N,N-dimethylaminopyridine. In general, reagents suitable for peptide synthesis will also be useful for the preparation of compounds of formula (IV).

In one embodiment, the compound having formula (II) is 10,12-pentacosadiynoic acid. In certain embodiments, the diamine compound having formula (III) may be selected from the group consisting of 1,2-diaminoethane, $N^1$-ethyl-1, 2-diaminoethane, and $N^1,N^1$-diethyl-1,2-diaminoethane. In still other embodiments, the activated derivative is an N-hydroxysuccinimidate ester. In yet another embodiment, the N-hydroxysuccinimidate ester is prepared by reaction of structure (II) with N-hydroxysuccinimide in the presence of a carbodiimide. Suitable carbodiimides include but are not limited to 1-[3-(dimethylamino)propyl]-3-ethylcarbodiimide and N,N'-dicyclohexylcarbodiimide. Suitable alkylating agents include but are not limited to methyl iodide, bromoethane, and 1-bromopropane.

In another aspect, the present invention provides a method of forming a nanotube, including the steps of: (a) adding a non-polar solvent to a solution containing a plurality of amphiphilic non-chiral single-chain diacetylenic compounds to form a reaction solution; (b) drying the reaction solution, thereby forming a primitive structure; (c) preparing a primitive structure solution containing the primitive structure; (d) sonicating the primitive structure solution; and (e) drying the primitive structure solution, thereby forming the nanotubes.

In one embodiment, the non-polar solvent may be hexane, heptane, or cyclohexane. In another embodiment, the reaction solution may contain dichloromethane, chloroform, or carbon tetrachloride. In yet another embodiment, the primitive structure solution may contain a solvent, such as, without limitation, $H_2O$, hexane, chloroform, and carbon tetrachloride. In still another embodiment, the method further includes a step of applying the primitive structure solution onto a substrate (e.g., a glass) before the step (e). In addition, at least one of the plurality of amphiphilic non-chiral single-chain diacetylenic compounds may be a compound having formula (I).

In addition, the present invention provides a method of forming a "nanocarpet" supramolecular assembly of nanotubes, including the steps of: (a) adding a non-polar solvent to an initiation solution, wherein the initiation solution contains a plurality of amphiphilic non-chiral single-chain diacetylenic compounds; (b) drying the initiation solution, thereby forming a primitive structure; (c) preparing a primitive structure solution containing the primitive structure; (d) sonicating the primitive structure solution; (e) treating the primitive structure solution with ultraviolet light (e.g., ultraviolet light having a wavelength of about 254 nm); (f) partially drying the primitive structure solution, thereby forming a secondary structure; (g) adding a secondary structure solvent to the secondary structure; and (h) drying the secondary structure, thereby forming the nanocarpet. In one embodiment, the secondary structure solvent may be chloroform, dichloromethane, carbon tetrachloride, ethyl acetate, or ethyl ether.

The present invention further provides a method of forming a nanocarpet, including the steps of: (a) partially drying an initiation solution containing a plurality of amphiphilic non-chiral single-chain diacetylenic compounds, thereby forming a intermediate structure; (b) adding an aqueous solution to the partially dried intermediate structure; (c) treating the intermediate structure with ultraviolet light or γ-ray irradiation; and (d) drying the intermediate structure, thereby forming the nanocarpet.

In addition, the invention provides an improved method for polymerization of the nanotubes, which comprises dispersing the nanotubes on a support surface prior to irradiation. This is an improvement over solution polymerization, which is difficult to carry out to completion, and provides high yields of polymerized nanotubes (PNTs).

Also provided is a method of destroying or inhibiting the growth or proliferation of a microorganism (e.g., a bacterium or a fungus), by contacting the microorganism with one or more nanotubes of the present invention.

Other feature and advantages of the present invention will become apparent from the following detailed description. It should be understood that the detailed description and the specific examples, while indicating the preferred embodiments of the invention, are given by way of illustration only. Various changes and modifications will be apparent to those skilled in the art, and remain within the spirit and scope of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
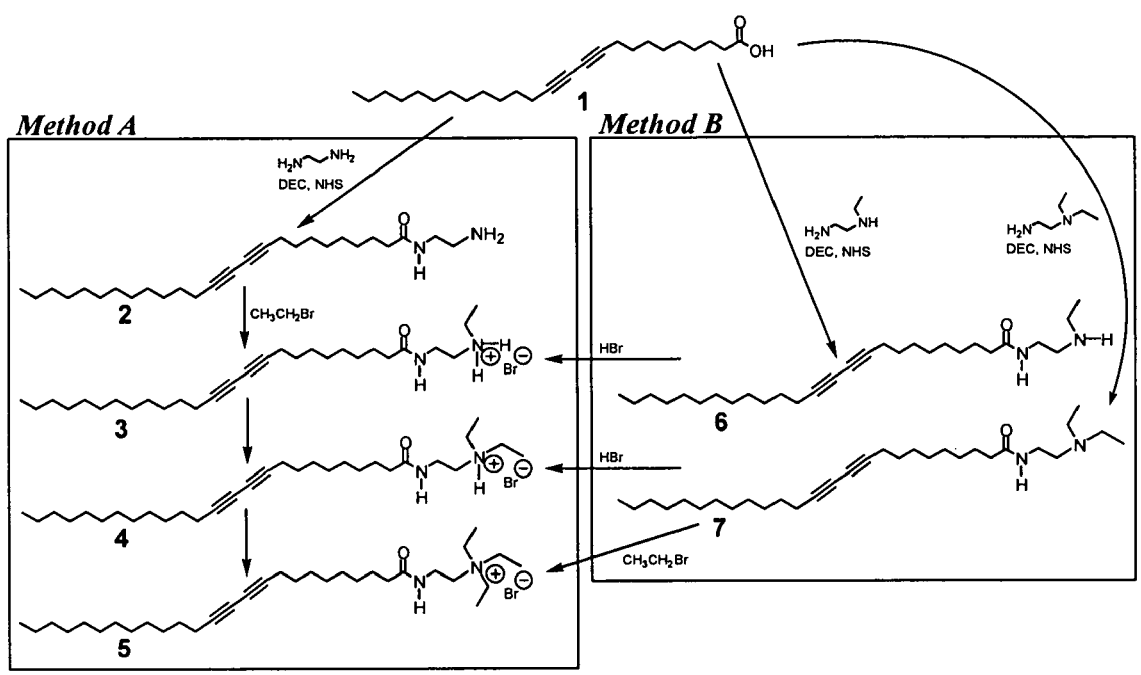
FIG. 1 illustrates the syntheses of 10,12-(pentacosadiynoy) l-N-ethylethylenediamine hydrobromide (compound 3), 10,12-(pentacosadiynoyl)-N,N-diethylethylenediamine hydrobromide (compound 4), 10,12-(pentacosadiynoyl)-N, N,N-triethylethylenediamine hydrobromide (compound 5), 10,12-(pentacosadiynoyl)-N-ethylethylenediamine (compound 6), and 10,12-(pentacosadiynoyl)-N,N-diethylethylenediamine (compound 7) in accordance with certain embodiments of the present invention.

As used herein and in the appended claims, the singular forms "a," "an," and "the" include plural references unless the content clearly dictates otherwise. Thus, for example, reference to "a diamine compound" includes a plurality of such diamine compounds and equivalents thereof known to those skilled in the art, and so forth, and reference to "the nanotube" is a reference to one or more such nanotubes and equivalents thereof known to those skilled in the art, and so forth. All publications, patent applications, patents, and other references mentioned herein are incorporated by reference in their entirety.

The present invention generally provides novel, amphiphilic non-chiral single-chain diacetylenic amphiphiles, and methods of synthesizing the same. The present invention also generally provides a method of producing nearly homogeneous monodisperse microstructures, such as, nanotubes (e.g., nanotubes with uniform diameter), nanocarpets, "nanocrackers," "nanohands," and the microstructures produced therewith. The remarkable self-assembly of these inexpensive and simple lipid compounds is unprecedented and represents a real step toward the rational design of nanostructured materials for a plethora of applications in fields, such as electronics, optics, biosensors, and pharmaceutics.

In one aspect, the present invention provides amphiphilic diacetylene compounds having formula (I):

$$W-C{\equiv}C-C{\equiv}C-V-L-QX \qquad (I)$$

wherein, the moiety W—C≡C—C≡C—V is a bilayer-compatible hydrophobic chain;

L is a linker comprising a chain of from 1 to 10 atoms;

Q is —$NR_2$ or —$NR'R_2^+$;

X is an anion, present only when Q is —$NR'R_2^+$;

each R is independently selected from the group consisting of H, $C_1$-$C_8$ alkyl and $C_6$-$C_{10}$ aryl; each R independently being unsubstituted or substituted with one or more substituents selected from the group consisting of halogen, oxo, acyl, alkenyl, alkoxyl, alkyl, alkylamino, amino, aryl, cycloalkyl, heterocyclyl, and heterocyclylalkyl, with the proviso that at least one R is not H; and R' is $C_1$-$C_8$ alkyl, optionally substituted with at least one selected from the group consisting of halogen, oxo, acyl, alkenyl, alkoxyl, alkyl, alkylamino, amino, aryl, cycloalkyl, heterocyclyl, and heterocyclylalkyl.

As used herein and in the appended claims, alkyl and alkenyl groups, as well as the alkyl and alkenyl moieties of other groups (e.g., alkoxy and alkylamino) may have up to eight carbon atoms, and they may be linear or branched, or comprise carbocyclic rings (e.g., isopropyl, t-butyl, cyclopentyl, cyclopropylmethyl, and the like). The term "aryl" encompasses phenyl, naphthyl, anthracenyl, and pyrenyl ring systems, and does not exclude the possibility of simple substituents. A heterocyclyl group may be any member of the group consisting of saturated, partially saturated, and unsaturated mono-, bi-, and tri-cyclic ring structures, having up to 14 ring atoms, wherein at least one atom of a ring is nitrogen, oxygen, or sulfur. The term "halogen" or "halide," as used herein and in the appended claims, includes fluorine (F), chlorine (Cl), bromine (Br), and iodine (I).

Bilayer-compatible hydrophobic chains are hydrocarbon chains of such a length that molecules of formula I will spontaneously self-assemble into bilayers at some temperature between about 0° C. and 100° C., when a solution of the compound is diluted with a non-solvent such as water or heptane. Hydrocarbon moieties that are too short do not experience sufficient van der Waals attractive forces to self-assemble, whereas chains that are too long will be disordered and the molecules will face an entropic barrier to alignment of the chains. Suitable candidates include but are not limited to linear hydrocarbon chains from about 8 to about 40 carbons in length. Preferably, the bilayer-compatible chain is between about 10 and about 30 carbons in length. The chains may optionally be modified, for example by halogenation or by incorporation of carbocylic rings, to modify their properties.

L is a "spacer" of from one to ten atoms in length. Suitable spacers include, but are not limited to, atom chains comprising $CH_2CH_2$, $CH_2CH_2CH_2$, $CH_2CH_2OCH_2CH_2$, $CH_2CH_2SCH_2CH_2$, $CH_2CH_2NHCH_2CH_2$ and $CH_2CH_2NRCH_2CH_2$, and may optionally incorporate keto, ester, or amide moieties. Preferably the spacer comprises an amide, and most preferably L is selected from CONHCH$_2$CH$_2$, CONHCH$_2$CH$_2$CH$_2$, CONHCH$_2$CH$_2$OCH$_2$CH$_2$, CONHCH$_2$CH$_2$SCH$_2$CH$_2$, and CONHCH$_2$CH$_2$NHCH$_2$CH$_2$.

In one embodiment, a is 10 and b is 7. Examples of the diacetylenic compounds of the present invention include, without limitation, N-(10,12-pentacosadiynoyl)-N'-ethylethylenediamine hydrobromide (compound 3), N-(10,12-pentacosadiynoyl)-N',N'-diethylethylenediamine hydrobromide (compound 4), N-(10,12-pentacosadiynoyl)-N',N',N'-triethylethylenediamine hydrobromide (compound 5), N-(10,12-pentacosadiynoyl)-N'-ethylethylenediamine (compound 6), and N-(10,12-pentacosadiynoyl)-N',N'-diethylethylenediamine (compound 7).

In another aspect, the present invention provides a method for preparing a compound having the formula (I), wherein W is CH$_3$(CH$_2$)a- and V is —(CH$_2$)b- and wherein a+b is from about 4 to about 30, which comprises reacting an activated derivative of a compound having formula (II):

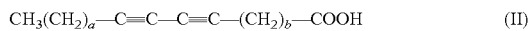

in a reaction mixture with a diamine compound having formula (III):

in the presence of a carboxylic acid activating reagent, thereby producing a compound having formula (IV):

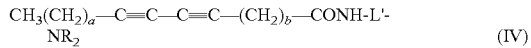

and, optionally, reacting the compound having formula (IV) with an alkylating agent R'—Y, thereby producing the compound of formula (V),

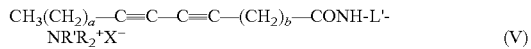

wherein,
a+b is from about 4 to about 30;
L' is selected from the group consisting of CH$_2$CH$_2$, CH$_2$CH$_2$CH$_2$, and CH$_2$CH$_2$ZCH$_2$CH$_2$;
where
Z is selected from the group consisting of CH$_2$, O, S, and NR;
X is a leaving group;
each R is independently selected from the group consisting of hydrogen, C$_1$-C$_8$ alkyl, and C$_6$-C$_{14}$ aryl, wherein each R is optionally substituted with at least one selected from the group consisting of halogen, oxo, acyl, alkenyl, alkoxyl, alkyl, alkylamino, amino, aryl, cycloalkyl, heterocyclyl, and heterocyclylalkyl; and
R' is C$_1$-C$_8$ alkyl, optionally substituted with at least one selected from the group consisting of halogen, oxo, acyl, alkenyl, alkoxyl, alkyl, alkylamino, amino, aryl, cycloalkyl, heterocyclyl, and heterocyclylalkyl.

In one embodiment, a novel diacetylenic compound of the present invention may be prepared by using the following process: a diacetylenic lipid having formula, CH$_3$(CH$_2$)$_m$C≡C—C≡C(CH$_2$)$_n$COOH (m=9, 11, or 13 and n=8 or 10), such as 10,12-pentacosadiynoic acid (PDA), may be converted to a succinimidyl ester in the presence of a N-hydroxysuccinimide (NHS) and a carbodiimide. Examples of carbodiimides include, but are not limited to, 1-[3-(dimethylamino)propyl]-3-ethylcarbodiimide (DEC) and N,N'-dicyclohexylcarbodiimide (DCC). Alternately, the diacetylenic acid may be converted to an acyl halide, for example by reacting with oxalyl chloride or thionyl chloride.

The modified diacetylenic lipids prepared as above may be slowly added to an excess amount of an appropriate diamine in a chlorinated solvent (e.g., chloroform and dichloromethane) or tetrahydrofuran. After the reaction, the mixture may be extracted with chloroform, dichloromethane, or ethyl acetate, and then washed with water. The organic phase may be dried with a drying agent (e.g., Na$_2$SO$_4$, MgSO$_4$, or CaCl$_2$) and evaporated (e.g., by using a rotary evaporator), typically yielding a white powder (e.g., compound 2 as shown in FIG. 1). The compounds may be further processed by quaternization at room temperature in a solvent, such as chloroform, nitromethane, or acetonitrile. The solvents may be removed by using a rotary evaporator to yield the desired diacetylenic compound (e.g., compounds 3, 4, and 5 as shown in FIG. 1).

In another embodiment, a novel diacetylenic compound of the present invention may be prepared using the following process: a diacetylenic lipid having formula, CH$_3$(CH$_2$)$_a$C≡C—C≡C(CH$_2$)$_b$COOH (a=9, 11, or 13 and b=8 or 10), such as, 10,12-pentacosadiynoic acid (PDA), converted to the NHS ester or acyl chloride, may be slowly added to an excess of an appropriate N-alkylalkylenediamine in a chlorinated solvent (e.g., chloroform or dichloromethane) or tetrahydrofuran. After the reaction, the mixture may be washed with water. The organic phase may be dried with a drying agent (e.g., Na$_2$SO$_4$, MgSO$_4$ or CaCl$_2$) and evaporated (e.g., by using a rotary evaporator) to yield the N-alkylalkylenediamine derivative of the diacetylenic lipid substrate (e.g., compound 6 as shown in FIG. 1). The compounds are further processed by reacting with a mineral acid, e.g., by adding HBr aqueous solution into an alcohol (e.g., methanol, ethanol, isopropyl alcohols), chlorinated solvent (e.g., chloroform and dichloromethane), or tetrahydrofuran solution of the N-alkylalkylenediamine derivative of the diacetylenic lipid substrate. The solvents may be removed by using a rotary evaporator to yield the desired diacetylenic compound (e.g., compounds 3 or 4, as shown in FIG. 1).

Figure 2:
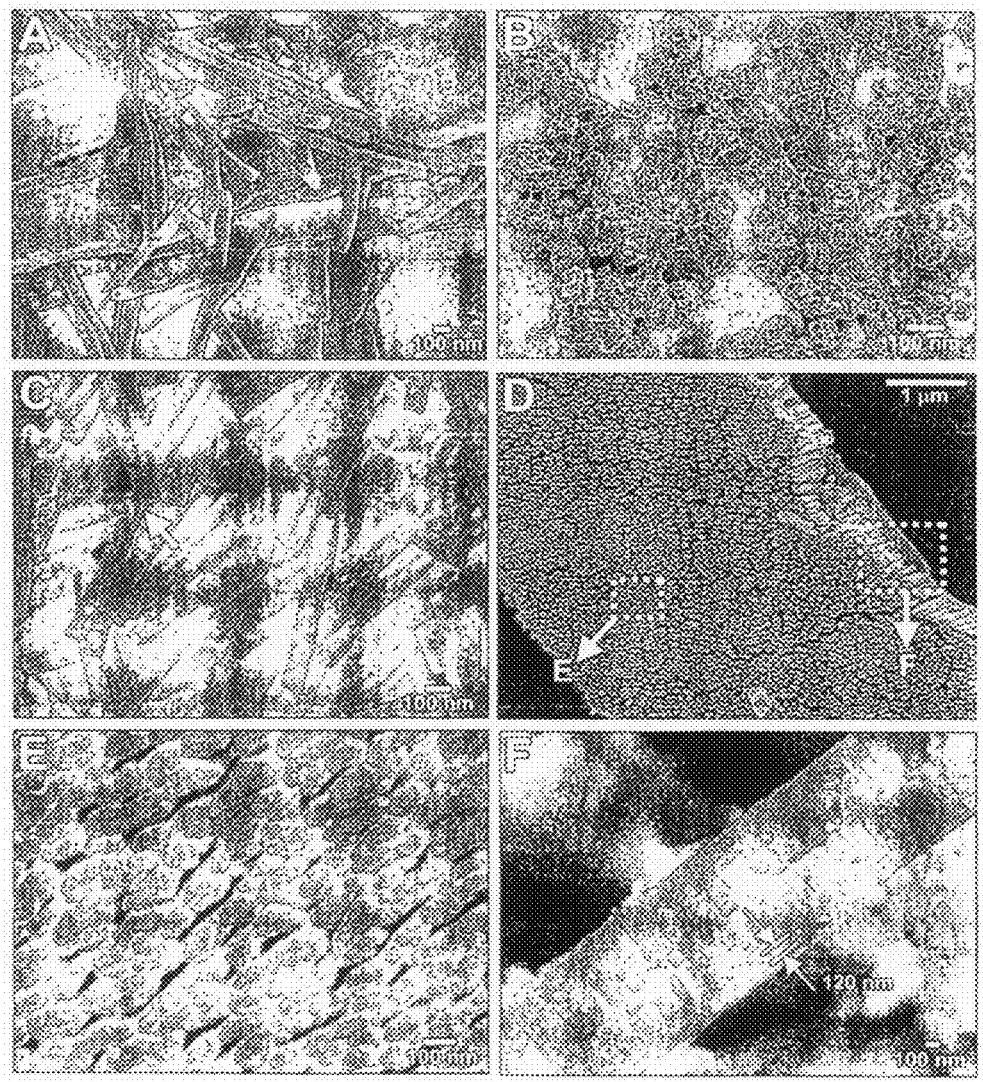
FIG. 2 shows scanning electron microscopy (SEM) images of nanotubes and nanocarpets formed in accordance with one embodiment of the present invention. (A) nanotubes and lamella structures; (B) lamella structures formed by the bromine salts of compound 2; (C) linear nanotubes and one branched nanotube formed by compound 3 showing the monodispersity of diameters; (D) a nanocarpet; (E) the front view of the nanocarpet of D; and (F) the side view of the nanocarpet of D.

The present invention further provides methods for producing a microstructure containing a plurality of amphiphilic non-chiral single-chain diacetylenic compounds, such as, compounds of the formula (I), and the microstructure produced therewith. As used herein and in the appended claims, the term "microstructure" includes a structure having at least one dimension within a range of about 0.5 nm to about 100 µm. In one embodiment, at least one dimension of the microstructure may be within a range of about 5 nm to about 1000 nm. In another embodiment, at least one dimension of the microstructure may be within a range of about 50 nm to about 500 nm. Examples of the microstructure include, without limitation, micrometer sized tubules, nanotubes, nanocarpets, nanocrackers, and nanohands. As used herein and in the appended claims, the terms "nanotube," "nanocracker," or "nanohand," refer to a tubular-shaped, a cracker-shaped, or a hand-shaped microstructure, respectively, having at least one dimension within a range of about 0.5-1000 nm, while the term "nanocarpet" refers to a microstructure having a plurality of clustered nanotubes. In one embodiment, at least one dimension of the nanotube, nanocarpet, nanocracker, or nanohand may be within a range of about 5 nm to about 800 nm. In another embodiment, at least one dimension of the microstructure may be within the range of about 50 nm to about 500 nm. Examples of the nanotubes, nanocarpets, nanocrackers, or nanohands are shown in FIG. 2.

In one aspect, the present invention provides a microstructure containing a plurality of nanotubes, wherein the nanotubes are of uniform diameter and are formed by self-assembly of one or more amphiphilic non-chiral single-chain diacetylenic compounds. As used herein in reference to an individual preparation of nanotubes, the term "uniform diameter" means that at least 95% of the nanotubes have a diameter within 10% and/or within 5 nm of the mean diameter of all the nanotubes in the composition.

For example, at least one of the amphiphilic non-chiral single-chain diacetylenic compounds may have the structure:

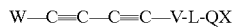

wherein the moiety W≡C—C≡C—V is a bilayer-compatible hydrophobic chain, L is a linker including a chain of from 1 to 10 atoms, and Q and X together are an ion pair. In one embodiment, W may be a $C_3$ to $C_{20}$ alkyl group. In another embodiment, V may be a $C_1$ to $C_{20}$ alkylene group. In yet another embodiment, L may be a —CONH(CH$_2$)$_m$— group and m is about 2-8. In still another embodiment, Q is a protonated secondary amine, such as, a —NH$_2$R$^+$ group, wherein R is a $C_1$-$C_8$ alkyl group.

In one aspect, the present invention provides a method of forming a nanotube, including: (a) adding a non-polar solvent to a plurality of amphiphilic non-chiral single-chain diacetylenic compounds (e.g., compounds having formula (I)) dissolved or suspended in a reaction solvent, e.g., dichloromethane; (b) drying the reaction solution, thereby forming a primitive structure; (c) preparing a primitive structure solution containing the primitive structure; (d) sonicating the primitive structure solution; and (e) drying the primitive structure solution, thereby forming the nanotubes. In one embodiment, the method further includes applying the primitive structure solution onto a substrate before the step (e). Examples of substrates suitable for the purpose of the present invention include, without limitation, a glass, a ceramic, a metal, a plastic, a polymer, and combinations thereof.

The non-polar solvent may be any suitable non-polar solvent known in the art, including, without limitation, hexane, heptane, cyclohexane, diethyl ether, and combinations thereof. In one embodiment, the ratio (v/v) of the non-polar solvent to the reaction solvent (e.g., dichloromethane) may be about 1:10. In another embodiment, such ratio is about 3:4. The resulting solution may be dried using standard techniques known in the art, such as, vacuum evaporation.

The primitive structure may be dissolved, completely or partially, in a solvent, such as, without limitation, water or water-based solution, dichloromethane, chloroform, carbon tetrachloride, tetrahydrofuran, ethyl acetate, N,N-dimethylformamide, acetone, alcohols, and combinations thereof, to form the primitive structure solution. As used herein and in the appended claims, the terms "solution" and "suspension" as applied to nanotube compositions includes homogenous and heterogeneous, aqueous and non-aqueous mixtures, in which a sufficient fraction of free and non-agglomerated nanotubes are present to carry out the desired transformation.

Any sonication system known in the art suitable for delivering sonic energy sufficient for the treatment of a solution may be used with the method of the present invention. Such devices may at times be referred to in the art as sonicators, ultrasonicators, sonic probes, or ultrasonic baths. A sonicator may contain a number of subsystems or affiliated systems, such as, without limitation, a programmable computerized control system and a temperature controlling system (e.g., a component which may function as a water bath). In one embodiment, a sonicator may be controlled, manually or by using a computerized control system, to operate in a continuous mode or a pulse mode. In another embodiment, for example, a sonication process may be conducted at 100 watts energy output, using continuous mode, in a water bath at room temperature. In yet another embodiment, a sonication process may be performed at any suitable frequency between about 5 kHz to 200 kHz.

The present invention provides for the dispersion of nanotubes on surfaces. Suitable surfaces include, but are not limited to, glass, ceramic, and metal surfaces, as well as polymer surfaces having suitable binding groups on the surface. Binding groups are groups capable of a binding interaction with the nanotubes, under the conditions in which the nanotubes are dispersed and attached to the surface. Suitable binding groups include, but are not limited to, hydroxyl, carboxyl, sulfhydryl, metal and silicon oxides and hydroxides, hydrocarbon, fluorocarbon, and electrically charged ionic species such as ammonium and phosphonium groups. The binding interaction may be, without limitation, hydrophobic, hydrogen-bonding, ion pairing, dipole-dipole, or covalent in nature, and will depend to a large extent on the functionality present on the exterior of the nanotubes. By way of example, a sulfhydryl group on the diacetylene precursor can be employed for covalent attachment to a gold surface, as is well-known in the art. Aluminum surfaces having an oxide coating may similarly be employed, and glass surfaces may be employed with or without surface functionalization, relying either on native SiOH groups or on introduced functional groups. Preferably the nanotubes are dissolved or suspended in a non-polar solvent and dispersed on a polar surface, and the surface is preferably glass.

In a typical example, a non-polar solvent is added to a vial containing diacetylene nanotubes and the vial is sonicated in an ultrasonic bath to detach the nanotubes from the walls of the container. Next, the liquid is transferred to a second container and fresh solvent is added followed by further sonication to disperse the nanotubes. A clean 25 mm×75 mm glass slide is placed in the resulting nanotube suspension to serve as a support surface, and the solution is agitated for 5 minutes to coat the glass slide with nanotubes. The nanotubes presumably attach themselves to the glass surface via electrostatic interactions between surface silicate anions and the quaternary or protonated amine in the diacetylene monomer head group, and/or by hydrogen-bonding interactions. The slide is then briefly rinsed with the same solvent and dried overnight in vacuo at room temperature.

Suitable non-polar solvents may be linear, branched, or cyclic, and include, but are not limited to, pentane, hexane, heptane, octane, isooctane, nonane, decane, cyclohexane, and the like, and mixtures thereof. Sonication is typically conducted in a water bath at room temperature. An ultrasonic bath with a power level of 100 W is suitable; the sonication method is preferably continuous rather than pulsed.

The surface-bound nanotubes are then exposed to radiation in order to initiate topochemical polymerization of the diacetylene moieties. Suitable radiation is any radiation known to induce diacetylene polymerization, and includes both UV and gamma radiation. Any UV- or gamma-radiation generating device known in the art to be suitable for polymerizing unsaturated compounds in solution may be used with the method of the present invention. The UV light may be filtered so that the device outputs UV light of a particular wavelength at a given time. In preferred embodiments, UV light having a wavelength of about 254 n1 is employed.

In another aspect, the present invention provides a method of forming a supramolecular assembly of nanotubes in the form of a "nanocarpet", including: (a) adding a non-polar solvent to an initiation solution, wherein the initiation solution contains a plurality of amphiphilic non-chiral single-chain diacetylenic compounds; (b) drying the initiation solution, thereby forming a primitive structure; (c) preparing a primitive structure solution (e.g., chloroform, dichloromethane, or carbon tetrachloride solution) containing the primitive structure; (d) sonicating the primitive structure solution; (e) treating the primitive structure solution with ultraviolet light (UV) or a γ-ray irradiation; (f) partially drying the primitive structure solution, thereby forming a secondary structure; (g) adding a secondary structure solvent (such as, without limitation, chloroform, dichloromethane, carbon tetrachloride, ethyl acetate, or ethyl ether) to the secondary structure; and (h) drying the secondary structure, thereby forming the nanocarpet. In one embodiment, the method further includes applying the primitive structure solution onto a substrate (e.g., glass) before the step (f). The term "partially drying," or "partially concentrating," generally refers to a process of eliminating about 60-90% of the solvent from a solution.

In yet another aspect, the present invention provides a method of forming a nanocarpet, including: (a) partially drying/concentrating an initiation solution (e.g., without limitation, a chloroform, dichloromethane, carbon tetrachloride, or ethyl acetate solution) containing a plurality of amphiphilic non-chiral single-chain diacetylenic compounds, thereby forming a intermediate structure; (b) adding $H_2O$ or an aqueous solution to the intermediate structure; (c) treating the intermediate structure with ultraviolet light or γ-ray irradiation; and (d) drying the intermediate structure, thereby forming the nanocarpet. In one embodiment, the method further includes applying the primitive structure solution onto a substrate (e.g., glass) before the step (a).

The present invention also provides a method of destroying or limiting/inhibiting the growth or proliferation of a microorganism, including contacting the microorganism with at least one nanotube which contains a plurality of amphiphilic non-chiral single-chain diacetylenic compounds (e.g., compounds of formula (I)). In one embodiment, a plurality of nanotubes may be polymerized (e.g., using UV light having a wavelength of about 254 nm) before contacting with the target microorganism. In another embodiment, the microorganism may include, without limitation, actinomycete, algae, archaeobacteria, cyanobacteria, gram-negative bacteria, gram-positive bacteria, fungi, and protozoa. In addition, the microorganism may be isolated, semi-isolated (e.g., in cell culture media), or unisolated (e.g., as a food contaminant or as a pathogen inside a subject (e.g., an animal, a human, or a plant)). Surfaces, including but not limited to the surfaces of implanted medical devices such as sutures, stents, and artificial joints and organs, may be rendered sterile and/or given microbicidal properties by coating them with the nanotubes or supramolecular assemblies of the present invention. Also provided by the invention are pharmaceutical compositions, containing a pharmaceutically-acceptable carrier and a compound of formula (I) and/or a nanotube which includes a plurality of compounds of formula (I).

The pharmaceutically-acceptable carrier may be "acceptable" in the sense of being compatible with the other ingredients of the composition, and not deleterious to the recipient thereof. The pharmaceutically-acceptable carrier employed herein may be selected from various organic or inorganic materials that are used in pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and/or viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The pharmaceutical composition of the present invention may be prepared by methods well-known in the pharmaceutical arts. For example, the composition may be brought into association with a carrier or diluent, as a suspension or solution. Optionally, one or more accessory ingredients (e.g., buffers, flavoring agents, surface active agents, and the like) also may be added. The choice of carrier will depend upon the route of administration of the composition. Formulations of the composition may be conveniently presented in unit dosage, or in such dosage forms as aerosols, capsules, elixirs, emulsions, eye drops, injections, liquid drugs, pills, powders, granules, suppositories, suspensions, syrup, tablets, or troches, which can be administered orally, topically, or by injection, including, without limitation, intravenous, intraperitoneal, subcutaneous, and intramuscular injection.

The pharmaceutical composition may be provided in an amount effective to treat a microorganism-induced disorder (e.g., an infectious disease) in a subject to whom the composition is administered. As used herein, the phrase "effective to treat the disorder" means effective to eliminate, ameliorate, or minimize the clinical impairment or symptoms resulting from the disorder.

In one embodiment of the present invention, the pharmaceutical composition may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump.

EXAMPLES

The following examples illustrate the present invention, which are set forth to aid in the understanding of the invention, and should not be construed to limit in any way the scope of the invention as defined in the claims which follow thereafter.

Example 1

Nanotubes Produced Using Mixtures of Compounds 2, 3, 4, and 5

The synthetic schemes are summarized in FIG. 1.

Compound 2 was produced when 3.0 g of 10,12-pentacosadiynoic acid (PDA) was converted to a succinimidyl ester by reaction with 2.77 g of N-hydroxysuccinimide (NHS) and 4.61 g of 1-[3-(dimethylamino)propyl]-3-ethylcarbodiimide (DEC) in chloroform (250 ml) for 12 hours. The resulting compound was added over the course of 30 minutes to 300 ml ethylene diamine-chloroform solution (6%, w/v). After reaction overnight at room temperature, the mixture was extracted with 250 ml of chloroform. The organic phase washed with distilled water (100 ml) for five times and dried with $NaSO_4$ and rotary evaporation to yield a white powder (compound 2).

Compound 2 (3 g) was then subjected to a quaternization reaction at room temperature by mixing with 5 ml of ethyl bromide in 15 ml of nitromethane. Reaction solvents were removed by a rotary evaporation and the resulting white solid was dissolved in a small amount (about 1-10 ml) of dichloromethane. Nanotubes were formed by first slowly adding a large excess (about 3 to 4 fold, v/v) of hexane to the dichloromethane solution and then drying in a vacuum apparatus at room temperature. The 10 mg of dried preparations were re-suspended in 20 ml of water or hexane followed by sonication for 5-30 minutes in a water bath at room temperature. The energy output of the sonicator was 100 w. The sonicated solution was spread on glass slides and dried for 3 hours at room temperature. Mass spectroscopy and NMR analysis revealed that the nanotubes contain a mixture of compounds 2, 3, 4, and 5.

Example 2

Nanotubes Produced Using the Secondary Amine Salt of PDA Alkylated with an Ethyl Head Group PDA (2.77 g) modified with NHS in the presence of DEC (as above) was slowly added to a 10 fold excess of N-ethyl-1,2-ethylenediamine in dichloroethane. After an overnight reaction, the mixture washed five times with 100 ml of water. The organic phase was dried with sodium sulfate and rotary evaporated to yield a white powder (compound 6, as shown FIG. 1 panel B).

Pure compound 3 was prepared from compound 6. Compound 6 (1.0 g) is dissolved in 20 ml of chloroform and an equal volume of aqueous HBr was added. The mixture was shaken vigorously to transfer the HBr to the organic phase. The organic phase was removed and concentrated in a rotary evaporator from 20 ml to 3 ml. Hexane (300 ml) was added to the chloroform solution to precipitate compound 3 and the precipitate was dried in vacuum at room temperature. To prepare nanotubes, the dried precipitate was suspended in 20 ml of water or hexane, dropped on glass surface, and allowed to dry. Under SEM the nanotubes were absolutely monodisperse in wall thickness (31 nm) and internal diameter (41 nm) (FIG. 2C).

Figure 3:
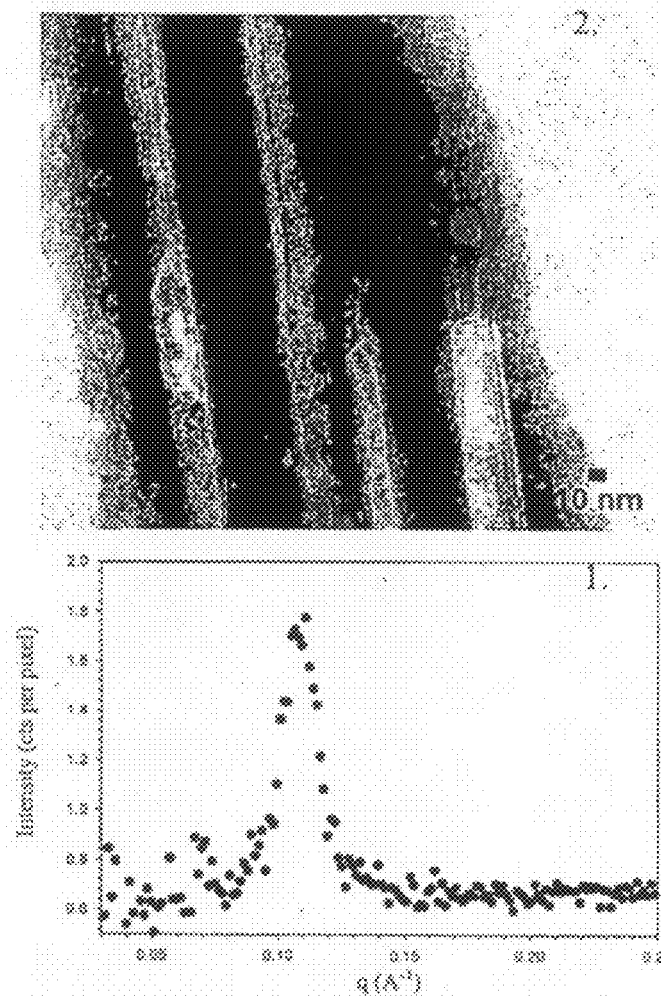
FIG. 3 shows a transmission electron microscopy (TEM) image of a nanotube showing (A) the five bilayer structures of the tubule walls; and (B) the small angle X-ray scatter (SAXS) analysis result of tubules formed from compound 3.
Figure 4:
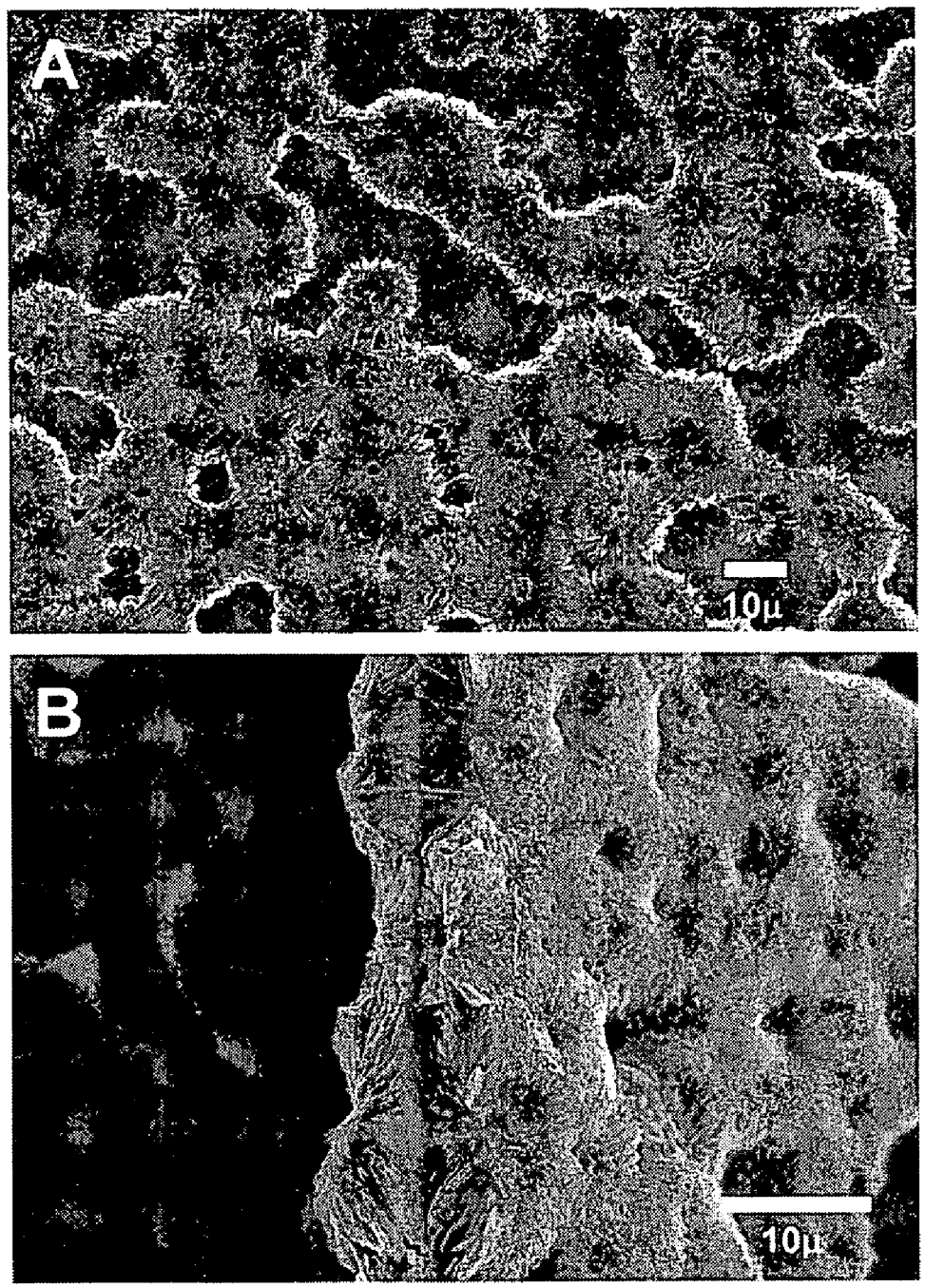
FIG. 4 shows SEM images of "nanocrackers" formed in accordance with one embodiment of the present invention.

The precise make up of these structures is provided by transmission electron microscopy (TEM). TEM of naked nanotubes and after staining with phosphotungstic acid reveals a hollow inner core and a wall consisting of 5 lipid bilayers (each bilayer is 43.1 Å across) (FIG. 3A). The structure in solution was further characterized by small angle X-ray scatter (SAXS) analysis. The results (FIG. 3B) suggest that the equilibrium spacing of the tubule bilayers in excess water is 57.9 Å. Although the diameter of the tubes was uniform throughout the sample, the length varied, with a mean of approximately 1 μm.

Example 3

Control of the Diameter of the Nanotube

PDA modified with NHS in the presence of DEC was slowly added to 10 times excess of N-propyl-1,2-ethylenediamine, or N-butyl-1,2-ethylenediamine, in dichloroethane, respectively. After the reaction, the mixture washed with water. The organic phase was dried with sodium sulfate and rotary evaporated to yield a white powder. The HBr amine salt of PDA alkylated with an n-propyl, or an n-butyl, head group and nanotubes made from the n-propyl derivatives of PDA or the n-butyl derivatives of PDA were prepared as described in Example 2. Under SEM the nanotubes were absolutely monodisperse in wall thickness (n-propyl PDA based nanotubes: 31 nm; n-butyl PDA based nanotubes: 33 nm) and internal diameter (n-propyl PDA based nanotubes: 34 nm; n-butyl PDA based nanotubes: 16 nm). The diameter of the nanotubes is uniform throughout the sample and the length varies from 200 nm to 1.8 μm.

Example 4

Nanocarpets Produced Using Mixtures of Compounds 2, 3, 4, and 5

The polydiacetylene nanocarpet composed of well-aligned nanotubes and its lamella structures was prepared without any external template. Using same method as used for the fabrication of nanotubes, 20 ml of primitive microstructure aqueous solution (0.05 mg/ml) was sonicated for 5 min (minutes) at 25° C. The diacetylene monomers were then polymerized by UV exposure (254 nm UV light) for 30 min at 5° C. The resultant solution (0.5 ml) was spread on a glass slide followed by drying for 1 hour at room temperature. At this time, which was before the complete drying of the sample, one drop of chloroform was added on the surface and the slide was allowed to dry for an additional 2 hours. The drying was followed by observation with the SEM. The nanocarpets in FIGS. 2D, 2E, and 2F were prepared without any external template. Microscopy shows that the pillars of the nanocarpet erupt from lamellar structures (FIGS. 2D and 2E) may be formed by the melting of one of the ends of the nanotubes. The inventors have observed the ability of chloroform at the junction of water/chloroform to "melt" nanotube ends in single nanotubes. Before exposure to chloroform the outer surface and inner surface of the nanotubes are hydrophilic and open-ended. The addition of a small amount of chloroform to a disordered surface of nanotubes may first melt the top surface of the tubes, creating a lamellar structure from which disoriented pillars could emerge. It is, perhaps, the gradual removal of chloroform that then causes the tubes to become aligned. The pillars of the resulting nanocarpet were approximately 100 nm in diameter and 1 μm in length (FIG. 2F). Each pillar consists of a cluster of 3-4 nanotubes of exactly the same diameter observed for the disordered nanotube systems described above. The carpet backing was about 120 nm thick (FIG. 2F).

Example 5

Nanocarpets Produced Using the Secondary Amine Salt of PDA (Compound 3) Alkylated with Ethyl Head Group The polydiacetylene nanocarpet was prepared without any external template. In the first experiment, the compound 3 (10 mg) was dissolved in 0.1 ml of chloroform. The solution was spread on a glass slide followed by drying for 1 hour at room temperature and 0.1 ml of water was added on the surface and the slide was allowed to dry for an additional 6 hours. The nanocarpets formed were followed by observation with the SEM.

The nanocarpets in FIGS. (4A and 4B) were prepared on a glass surface. Microscopy showed that the pillars of the nanocarpet erupted from lamellar structures. The pillars of the resulting nanocarpet were approximately 5 μm in thickness.

Example 6

Control of Nanotubes Length

Figure 5:
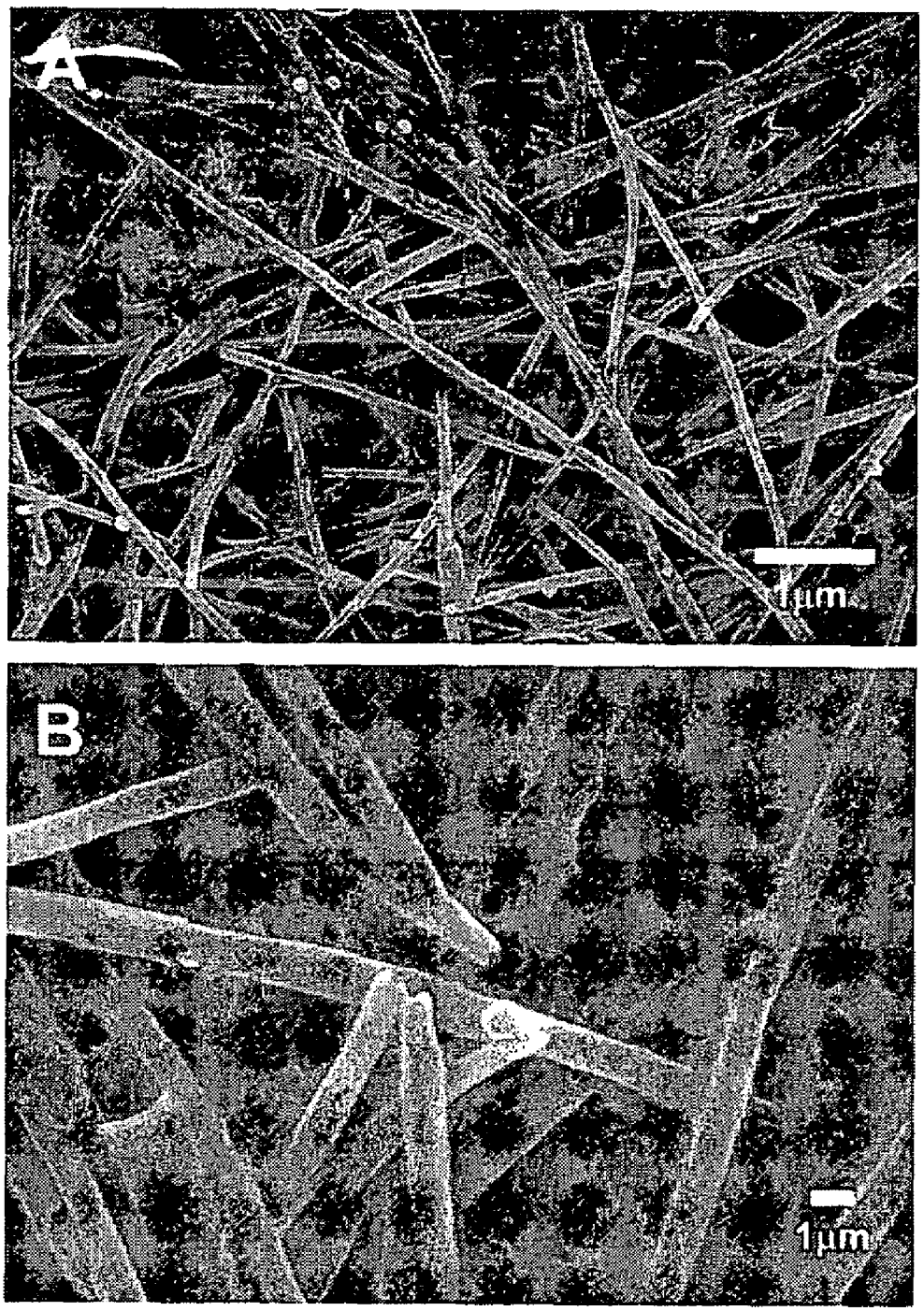
FIG. 5 shows SEM images of nanotubes formed in accordance with one embodiment of the present invention.

Secondary amine salt of PDA (compound 3) (1 mg/ml) alkylated with ethyl head group was placed in a glass test tube. The insoluble sample was carefully heated to a boil with a heat gun. At about 80° C., the secondary amine salt of PDA solution was clear. The solution was allowed to cool to room temperature and then placed in a chamber maintained at 4° C.

for 1 week before characterization. Under SEM the nanotubes are absolutely monodisperse in wall thickness (27 nm) and internal diameter (41 nm). The diameter of the nanotubes is uniform throughout the sample, the length varies from 15 µm to 20 µm as shown in FIG. 5.

Example 7

Antimicrobial Activity of the Nanotubes

Experiments were performed to assess the interaction of nanotubes with bacteria. The antimicrobial activity was tested by incubation of $2\times10^5$ *Escherichia coli* in a solution containing 10 µg/ml nanotubes. *E. coli* K12 were grown overnight in Luria broth, diluted in 0.3 mM potassium phosphate (pH 7.2), and used for either microscopy or in antimicrobial assays. For the antimicrobial assay 1 ml of a suspension containing $5\times10^5$ cells was mixed with 1 ml of a solution of nanotubes. The mixture was shaken at 37° C. for 1 hour at which time samples were serially diluted and plated on Luria-agar plates to obtain viable counts. This treatment killed 99.98% of the *E. coli* cells within one hour.

Exposure of diacetylene molecules to UV light results in the formation of cross links between the molecules forming a polymeric chromogenic material. UV exposure of nanotubes in solution results in a color change from white to dark blue. When cross-linked nanotubes were mixed with bacteria, the material acted as a flocculent precipitating the cells and the nanotubes, while the color of the solution changes from dark blue to light blue.

Figure 6:
FIG. 6 shows TEM images of nanotubes mixed with *E. coli* cells in accordance with one embodiment of the present invention.
Figure 6:

The flocculation behavior was investigated by electron microscopy. A solution of nanotubes was prepared and mixed with a suspension of *E. coli*. TEM grids were dipped in the mixture, excess liquid was wicked off, and the grids were observed with the TEM. In these preparations the majority of the nanotubes were seen associated with the outer surface of the bacteria. FIG. 6 shows an example of a nanotube that is fused with the outer surface of the bacterial cell and a cell that has been enveloped by nanotube material.

Example 8

Adsorption of Nanotubes onto Surfaces

Figure 7:
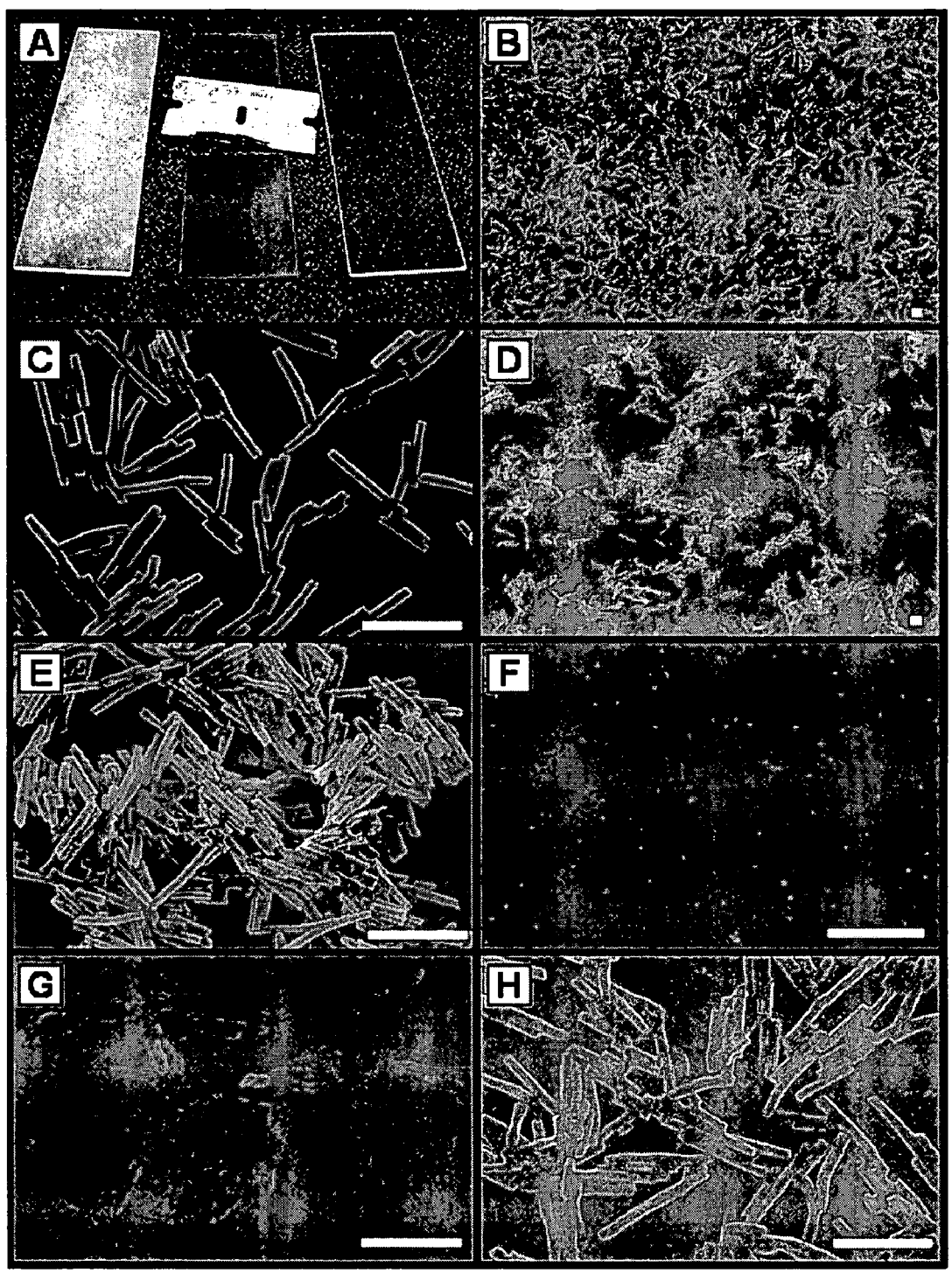
FIG. 7 shows (A) Nanotubes on glass slides: (left) unpolymerized nanotubes; (middle) polymerized nanotubes; (right) plain glass slide. (B) and (C) SEMs of nanotubes deposited on slides by dipping followed by sonication; (D) and (E) SEMs of nanotubes deposited by dipping without sonication. (F) Nanotube stability as a function of polymerization time: chloroform treatment of unpolymerized nanotubes; (G) chloroform treatment after 3 min polymerization; (H) chloroform treatment after 5 min. polymerization (scale bar, 1 μm).

Glass slides (25 mm×75 mm) were cleaned by soaking in 1:2 hydrogen peroxide-sulfuring acid ("piranha solution"). Hexane (20 mL) was added to a vial containing dried diacetylene nanotubes (10 mg) and the vial was sonicated in a sonic bath at room temperature for 5 min to detach the NTs from inside of the vial. Next, the hexane solution was transferred to a 250 mL glass bottle and fresh hexane (230 mL) was added followed by another 5 min sonication at room temperature to disperse the nanotubes. A clean, dry glass slide was placed in the nanotube suspension and either gently shaken at 100 rpm on a rotary shaker for 5 minutes, or sonicated for 5 minutes, to coat the glass slide with nanotubes. After the shaking or sonication was complete, the glass slide was again transferred to a 250 ml glass bottle containing fresh hexane (230 mL). The slide was rinsed for 5 minutes and dried overnight in a vacuum oven at room temperature. Unpolymerized nanotubes coating the surface are shown in FIG. 7A (left slide). The tendency of the nanotubes to clump is evident during dip coating without sonication (FIGS. 7D and 7E) but is significantly reduced when accompanied by sonication (FIGS. 7B and 7C).

Example 9

Polymerization of Nanotubes on Glass Slides

Glass slides (25 mm×75 mm) were coated with nanotubes as described above. One side of a slide was wiped clean with tissue paper soaked with methanol, so that only one side of the slide had nanotubes on the surface. The slide was then placed in a UV-crosslinker (Spectrolinker XL-1000 Spectronics Corp., Westbury, N.Y.). The nanotube-containing surface faced a 6100 mW/cm2 low-pressure mercury lamp, with maximum emission at 254 nm, positioned 15 cm above the glass slide. At 1 min intervals, the absorbance spectrum of the nanotubes was measured on a Perkin-Elmer model Lambda 45 spectrophotometer. The nanotube coating rapidly developed the blue color characteristic of diacetylene polymers (FIG. 7A, center slide), and polymerization was complete after 5 min.

Example 10

Polymerization of Nanotubes in Solution

A nanotube solution (10 mg of nanotubes in 100 mL of either hexane or water) was placed in a beaker (80 mm in diameter and 40 mm in height). The beaker was placed in the UV-crosslinker and agitated with a mechanical stirrer. At 1 min intervals, 1.2 mL aliquots were removed from the beaker and the absorbance spectrum was measured on the UV spectrophotometer. The loss of solvent during the polymerization was compensated for by adding fresh hexane or water.

The extent of polymerization was followed by measuring the increase in optical density at 625 nm. As has been shown previously (R. M. Jisr et al., *Angew. Chem. Int. Ed. Engl.* (2005) 44:782-785), there are competing effects of UV irradiation on the polymerization, in that extended exposure causes breakage and rearrangement of the cross linking bonds. This side reaction can be monitored by an increase of absorption at 525 nm at the expense of that at 625 nm. The $OD_{625}$ reached a maximum and then decreased, whereas the peak at 525 nm began to appear after a few minutes and continued to increase. Polymerization of nanotubes reached a peak after approximately 10 minutes' exposure to UV, after which the disruptive reaction began to dominate. Additionally, observation of the suspension showed that there was a noticeable clumping of the nanotubes during polymerization.

The integrity of the solution-polymerized nanotubes was assessed by exposure to chloroform. The solvent melted these sparsely polymerized nanotubes, confirming that polymerization was incomplete and unable to dramatically harden these remarkable structures.

Example 11

Exposure of Nanotubes to Heat and Solvents

Thermal stability was analyzed using a differential scanning calorimeter (DSC). Unpolymerized nanotubes and nanotubes polymerized for various times (1.5 mg) were dispersed in hexane, placed in an aluminum DSC cell, and allowed to dry in a vacuum oven for 24 h at 25° C. The DSC cell was placed on a differential scanning calorimeter (Shimadzu DSC 60) under a helium purge. Scanning rates of 10°

C./min were used over a temperature range of 25° C. to 140° C. In this way the melting temperature of unpolymerized nanotubes was determined to be 108.9° C. By comparison, the diacetylene acid precursor to NFM-1 has a melting point of 63.6° C., and the immediate precursor to NFM-1, the secondary amine, has a melting point of 59.4° C. The polymerized nanotubes, on the other hand, do not show a melting temperature and resist a change in structure upon heating. The peak at 79.5° C. in the DSC of unpolymerized nanotubes is due to intermolecular hydrogen bonding (H. E. Huggins et al., *Macromolecules* (1997), 30:5305-5312). The disappearance of this peak when the nanotubes are polymerized is likely due to the fact that the covalently-bound lipid molecules in a tightly packed diacetylene tube do not separate upon a temperature increase, and the intermolecular hydrogen bonds therefore remain intact.

Figure 9:
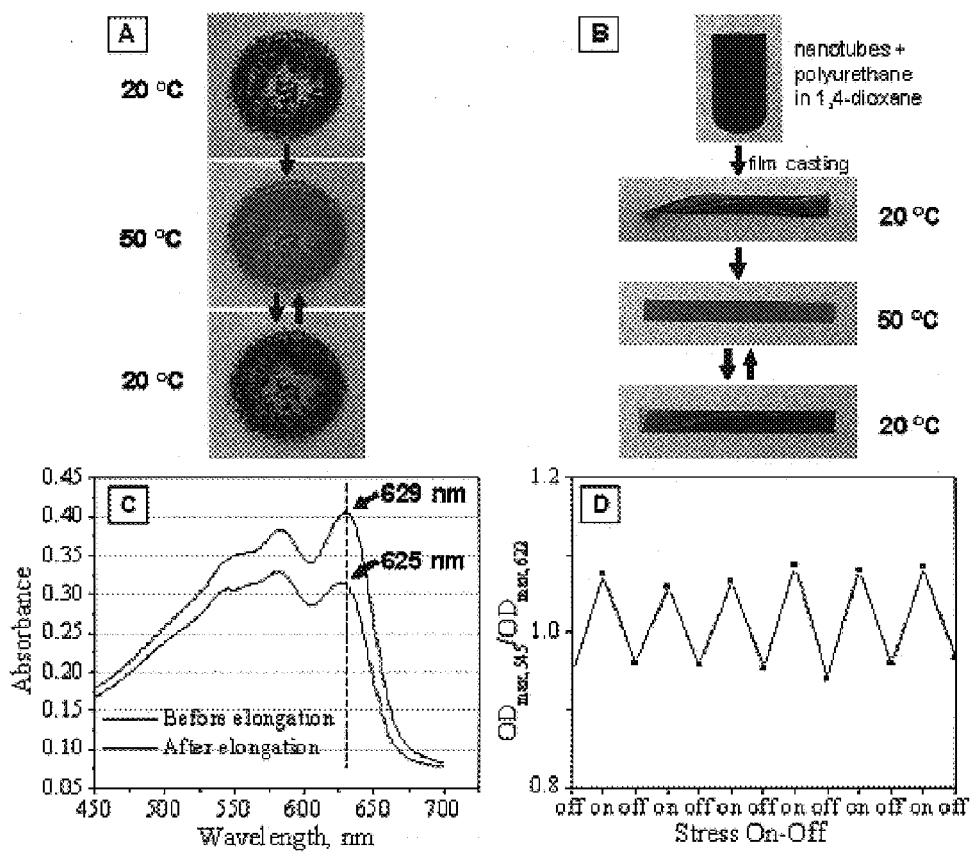
FIG. 9 depicts thermochromism and mechanochromism of polymerized nanotubes. Thermochromism of polymerized nanotubes: (A) dried on a glass slide; (B) in polyurethane. Mechanochromism of polymerized nanotubes embedded in polyurethane elastomer: (C) UV absorption before and after elongation; (D) reversible on-off behavior of the nanotubes embedded in a polyurethane elastomer.

The polymerized nanotubes, spotted on a glass slide, were deep blue at room temperature, as seen in FIG. 9A (top). When heated above 44° C., they rapidly transitioned to a bright red color, returning to blue upon cooling (FIG. 9A, center and bottom). The thermochromic behavior was stable, and the temperature could be cycled repeatedly between 20° C. and 60° C. without any loss in the speed or intensity of the color change.

Figure 8:
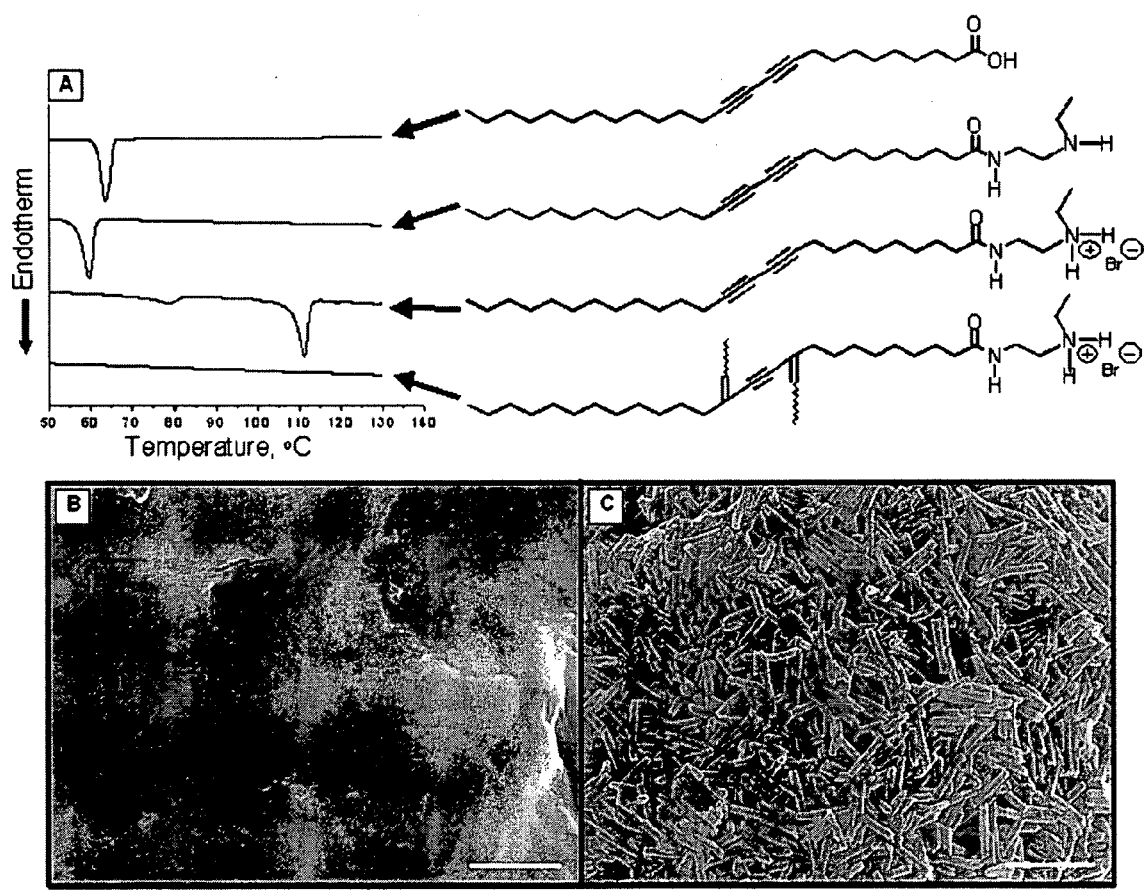
FIG. 8 depicts (A) DSC scans of unpolymerized and polymerized nanotubes, and precursor lipid. Heat resistance of unpolymerized (B) and polymerized (C) nanotubes. Scale bar, 1 μm.

To determine the stability of the nanotubes at high temperature, the unpolymerized and polymerized nanotubes were placed on a hot stage (140° C.) for 10 seconds, and then sputter coated with 3.5 nm coating of gold/palladium (Cressington 108 auto sputter coater, Cressington Scientific Instruments Ltd., Watford, UK). Samples were viewed in a JEOL JEM-6335F scanning electron microscope (JEOL, Peabody, Mass., USA) at 10 kV. Polymerization hardens the tubes to such a degree that exposure to 140° C. does not change the structure (FIG. 8C), whereas the unpolymerized nanotubes disassociate into an amorphous mass (FIG. 8B) after exposure to the same temperature.

For determination of solvent stability, chloroform was added to the unpolymerized and polymerized nanotubes on glass slides prior to SEM. The resistance of the polymerized nanotubes (PNTs) to disruption by chloroform is time-dependent, increasing as the degree of polymerization increase. Unpolymerized nanotubes are completely dissolved by chloroform (FIG. 7F). After 3 minutes of irradiation the nanotubes have obtained a small level of resistance to chloroform (FIG. 7G), and after 5 minutes of UV exposure the nanotubes are fully chloroform-resistant (FIGS. 7A (center slide) and 7H).

While the foregoing invention has been described in some detail for purposes of clarity and understanding, it will be appreciated by one skilled in the art, from a reading of the disclosure, that various changes in form and detail can be made without departing from the true scope of the invention in the appended claims.

Note: The patent or application file contains at least one drawing executed in color. Copies of this patent or patent application publication with color drawing(s) will be provided by the Office upon request and payment of the necessary fee.

We claim:

1. A compound having formula (I):

W—C≡C—C≡C—V-L-Q X    (I)

wherein
    the moiety W—C≡C—C≡C—V is a bilayer-compatible hydrophobic chain, wherein W is $CH_3(CH_2)_a$— and V is —$(CH_2)_b$—; where a+b is from about 4 to about 40;
    L is a linker comprising a chain of about 1-10 atoms;
    Q is —$NH_2R^+$;
    X is an anion;
    R is selected from the group consisting of $C_1$-$C_8$ alkyl and $C_6$-$C_{10}$ aryl; R being unsubstituted or substituted with one or more substituents selected from the group consisting of halogen, oxo, acyl, alkenyl, alkoxyl, alkyl, alkylamino, amino, aryl, cycloalkyl, heterocyclyl, and heterocyclylalkyl.

2. The compound of claim 1, wherein R is $C_1$-$C_8$ alkyl.

3. The compound of claim 1, wherein L is selected from the group consisting of $CONHCH_2CH_2$, $CONHCH_2CH_2CH_2$, and $CONHCH_2CH_2ZCH_2CH_2$; wherein Z is selected from the group consisting of $CH_2$, O, S, and NR.

4. The compound of any of claims 1, wherein W is $CH_3(CH_2)_a$— and V is
    —$(CH_2)_b$—; where a+b is from about 4 to about 30.

5. The compound of claim 4, wherein a=1 and b=8.

6. The compound according to claim 1, wherein the compound is N-(10,12-pentacosadiynoyl)-N',N'-diethylethylenediamine hydrobromide.

7. A nanotube comprising at least one amphiphilic non-chiral single-chain diacetylenic compound having a structure:

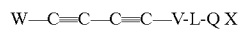

wherein W—C≡C—C≡C—V is a bilayer-compatible hydrophobic chain, L is a linker comprising a chain of from about 1 to about 10 atoms, Q and X together are an ion pair, W is a $C_3$ to $C_{20}$ alkyl group, V is a $C_1$ to $C_{20}$ alkylene group, and Q is a protonated secondary amine.

8. The nanotube of claim 7, wherein L is a —CONH$(CH_2)_m$— group and m is about 2-8.

9. The nanotube of claim 7, wherein Q is a —$NH_2R^+$ group and R is a $C_1$-$C_8$ alkyl group.

10. The nanotube of claim 7 further comprising a second amphiphilic non-chiral single-chain diacetylenic compound having a structure:

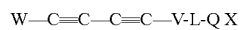

wherein W—C≡C—C≡C—V is a bilayer-compatible hydrophobic chain, L is a linker comprising a chain of from about 1 to about 10 atoms, Q and X together are an ion pair, W is a $C_3$ to $C_{20}$ alkyl group, V is a $C_1$ to $C_{20}$ alkylene group, and Q is a protonated secondary amine.

11. A composition comprising a plurality of nanotubes formed by self-assmebly of one or more amphiphilic non-chiral single-chain diacetylenic compounds having a structure:

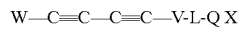

wherein W—C≡C—C≡C—V is a bilayer-compatible hydrophobic chain, L is a linker comprising a chain of from about 1 to about 10 atoms, Q and X together are an ion pair, W is a $C_3$ to $C_{20}$ alkyl group V is a $C_1$ to $C_{20}$ alkylene group and Q is a protonated secondary amine.

12. The composition of claim 11, wherein said nanotubes are of uniform diameter.

13. The composition of claim 11, wherein the nanotubes are aligned in a supramolecular assembly.

14. The composition of claim 13, wherein the supramolecular assembly is a nanocarpet.

15. The composition of claim 11, wherein L is a —CONH$(CH_2)_m$— group and m is about 2-8.

16. The composition of claim 11, wherein Q is a —$NH_2R^+$ group and R is a $C_1$-$C_8$ alkyl group.

* * * * *

UNITED STATES PATENT AND TRADEMARK OFFICE
CERTIFICATE OF CORRECTION

PATENT NO. : 7,666,911 B2  
APPLICATION NO. : 11/237838  
DATED : February 23, 2010  
INVENTOR(S) : Russell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1086 days.

Signed and Sealed this

Seventh Day of December, 2010

David J. Kappos  
*Director of the United States Patent and Trademark Office*